(12) United States Patent
Andersen et al.

(10) Patent No.: US 12,303,601 B2
(45) Date of Patent: May 20, 2025

(54) METHODS OF FABRICATION OF CONCENTRATED AND HOMOGENEOUSLY WETTED MASSIVE POLYMERS AND APPLICATIONS THEREOF

(71) Applicant: SolyPlus GmbH, Haselund (DE)

(72) Inventors: Richard Dolph Andersen, Berlin (DE); Annette Assogba-Zandt, Berlin (DE); Elena Maltseva, Schöneiche (DE); Andreas Voigt, Berlin (DE)

( * ) Notice: Subject to any disclaimer, the term of this patent is extended or adjusted under 35 U.S.C. 154(b) by 890 days.

(21) Appl. No.: 16/753,463

(22) PCT Filed: Oct. 9, 2018

(86) PCT No.: PCT/IB2018/057789
§ 371 (c)(1),
(2) Date: Apr. 3, 2020

(87) PCT Pub. No.: WO2019/073362
PCT Pub. Date: Apr. 18, 2019

(65) Prior Publication Data
US 2020/0253876 A1 Aug. 13, 2020

(30) Foreign Application Priority Data
Oct. 12, 2017 (DE) .......................... 102017009767.4

(51) Int. Cl.
*A61K 9/14* (2006.01)
*A61K 47/36* (2006.01)

(52) U.S. Cl.
CPC .............. *A61K 9/146* (2013.01); *A61K 47/36* (2013.01)

(58) Field of Classification Search
CPC ...... A61K 9/146; A61K 47/36; A61K 9/0021; C08B 37/0072; C08L 5/08
See application file for complete search history.

(56) References Cited

U.S. PATENT DOCUMENTS 5,980,946 A * 11/1999 Jones .................. A61P 9/00
424/484
2010/0228203 A1 * 9/2010 Quan ................ A61M 37/0015
604/272
2012/0295869 A1 * 11/2012 Liu .................... A61P 27/02
514/54

FOREIGN PATENT DOCUMENTS

| CA | 795689 A | 10/1968 | |
|---|---|---|---|
| CN | 107233217 A | 10/2017 | |
| WO | WO-9702845 A1 * | 1/1997 | ........... A61L 15/225 |

OTHER PUBLICATIONS

Communication pursuant to Article 94(3) EPC issued on Mar. 29, 2022, in connection with corresponding European Application No. 18796115.6; 7 pages.

* cited by examiner

*Primary Examiner* — Monica A Shin

(57) ABSTRACT

Embodiments described herein generally relate to methods of homogeneous wetting of biopolymers, derivatives therefrom and synthetic polymers, and, their applications.

20 Claims, 2 Drawing Sheets

Figure 1 mixing of at least one biopolymer, ice in microparticular form, and optionally at least one active pharmaceutical ingredient by means of mechanical energy input to obtain a homogenous mixture at a temperature below the freezing point of water

further mixing the at least one biopolymer, ice in microparticular form, and optionally the at least one active pharmaceutical ingredient with a steady increase of temperature above the freezing point of water

further kneading/mixing to produce a homogeneously wetted biopolymer

Figure 2 mixing of at least one biopolymer in dry form, ice produced by freezing water, dry ice ($CO_2$), and optionally at least one active pharmaceutical ingredient by means of mechanical energy input to obtain a homogeneous microparticular mixture of all ingredients at temperatures above the freezing temperature of dry ice and below the freezing temperature of water ice

further mixing with a steady increase of temperature above the freezing point of water

further kneading/mixing of the homogeneously wetted mixture

METHODS OF FABRICATION OF CONCENTRATED AND HOMOGENEOUSLY WETTED MASSIVE POLYMERS AND APPLICATIONS THEREOF

PRIORITY CLAIM

This PCT International Patent Application herein claims priority to German priority patent application serial number 102017009767.4, filed Oct. 12, 2017, the entire contents of which are incorporated herein in its entirety.

FIELD OF THE INVENTION

Embodiments described herein generally relate to methods of homogeneous wetting of biopolymers, derivatives therefrom and synthetic polymers, and their applications.

BACKGROUND

For hundreds or even thousands of years mankind has developed cosmetical, pharmaceutical and nutritional preparations for internal and external uses, treatments and applications. These preparations contain passive as well as active ingredients. The group of biopolymers and derivatives therefrom provides diverse examples for both, active (for example, antibodies, enzymes, nucleic acids, complex compounds of proteins and nucleic acids) as well as passive (for example, collagen, dextran, hyaluronic acid) ingredients. Furthermore, there are included into these developments derivatives of biopolymers (for example, cellulose derivatives, gelatin, chitosan) and also synthetic polymers (for example, derivatives of acrylates).

In general, the presence of polymers is enabling for, or useful in modifying, the delivery of active pharmaceutical ingredients (APIs). Other have made continuous efforts to offer new and improved technical solutions based on modified polymers. As a fundamental aspect of polymer-based development efforts, there has to be an availability of polymer ingredients of excellent quality and sufficient quantity based on industry guidelines.

Procedures and methods have to take into account the chemical and physico-chemical peculiarities of the polymers. The macromolecular character as well as the tendency to form aggregates during all phases of formulation make it necessary to use special and adapted methods to meet the high qualities/standards of industries and consumers.

Many conventional approaches at developments based on polymers fail to adequately consider interactions with the used solvent. Based on conventional approaches by others, there are several problems associated with such conventional approaches. There are frequently observed formation of aggregates in dilute systems, and in more concentrated systems, inhomogeneous wetting, inclusion of gas/air and derived therefrom optical and mechanical properties, porosities, etc. In aqueous systems, the extent of such effects depends on the strength of hygroscopic polymer properties. There are observed similar and comparable effects in non-aqueous solvents.

As a rule, an inhomogeneous wetting of massive polymers (powder at process start) which have to be formulated at high concentration (plastic mass) cannot or nearly not be completely corrected downstream.

Other have made attempts at the industrial fabrication of concentrated polymer masses (massive plastics), especially of biopolymer masses. The first industrial example was the milk protein casein. Previous attempts at the fabrication and application of massive casein plastic masses (art horn) have involved, for example, means of a process chain comprising wetting, kneading, shaping, and fixation.

Besides art horn, casein was also used as a coating material, as an ingredient in the paper industry, in the glue industry, in medicine, in the nutrition industry, in photography, in soap fabrication, in leather and textile industries and as conditioner for delivery of chemicals. Casein was also formulated as composite with gelatin, cellulose and kaolin.

In view of all of the limitations, disadvantages and problems associated with conventional approaches that have been used by others, there is a significant, long-felt and yet unmet need for improved methods of homogeneous wetting of biopolymers, derivatives therefrom and synthetic polymers, and their applications.

SUMMARY OF REPRESENTATIVE EMBODIMENTS OF THE INVENTION

It is to be understood that the present invention contemplates certain representative methods and formulations, such as for example certain methods and formulations described herein, in which at least one active pharmaceutical ingredient is present.

It is also to be understood that the present invention also contemplates other representative methods, processes and formulations in which no active pharmaceutical ingredients are present or used at any point during the methods or processes, and therefore the present invention also contemplates formulations in which no active pharmaceutical ingredients are present in the final formulations. Therefore, when certain representative methods, processes and formulations are described herein, it is also to be understood that the present invention also contemplates that such methods, processes and formulations can be adapted or modified in an appropriate and suitable manner, as needed or desired, such that no active pharmaceutical ingredients are present or used at any point during the methods or processes, such that no active pharmaceutical ingredients are present in the final formulations.

Therefore it is to be understood that the methods and processes of the present invention, of which several examples are described herein, can be practiced and implemented in such a manner such that including at least one active pharmaceutical ingredient is optional.

According to one representative embodiment, the present invention provides a method of homogeneous wetting of at least one biopolymer, comprising: mixing of at least one biopolymer, ice in microparticular form, and optionally at least one active pharmaceutical ingredient by means of mechanical energy input to obtain a homogenous mixture at a temperature below the freezing point of water; further mixing the at least one biopolymer, ice in microparticular form, and optionally the at least one active pharmaceutical ingredient with a steady increase of temperature above the freezing point of water; and further kneading/mixing to produce a homogeneously wetted biopolymer.

According to another representative embodiment, the present invention provides a method of homogeneous wetting of at least one biopolymer, comprising: mixing of at least one biopolymer and ice in microparticular form, by means of mechanical energy input to obtain a homogenous mixture at a temperature below the freezing point of water; further mixing the at least one biopolymer and ice in microparticular form, with a steady increase of temperature above the freezing point of water; and further kneading/mixing to produce a homogeneously wetted biopolymer.

According to another embodiment, the present invention provides a method of homogeneous wetting of at least one biopolymer, comprising: mixing of at least one biopolymer in dry form, ice produced by freezing water, dry ice ($CO_2$), and optionally at least one active pharmaceutical ingredient by means of mechanical energy input to obtain a homogeneous microparticular mixture of all ingredients at temperatures above the freezing temperature of dry ice and below the freezing temperature of water ice; further mixing with a steady increase of temperature above the freezing point of water; and further kneading/mixing of the homogeneously wetted mixture.

As described herein, it is to be understood that in certain embodiments the present invention contemplates that the temperature can be controlled by the interplay of dry ice, water ice and heat production via mechanical input. However, it is also to be understood that the present invention also contemplates that the temperature can be controlled in other embodiments by the use of liquid nitrogen for cooling purposes. Moreover, the present invention also contemplates that, in addition to liquid nitrogen, any other appropriate and suitable cooling substance can also be used which helps to control the temperature well below water's freezing point.

According to one embodiment, a method of homogeneous wetting of at least one biopolymer, comprises: mixing of at least one biopolymer in dry form, ice produced by freezing water, dry ice ($CO_2$) or liquid nitrogen or any other cooling substance and optionally at least one active pharmaceutical ingredient by means of mechanical energy input to obtain a homogeneous microparticular mixture of all ingredients at temperatures above the freezing temperature of dry ice or liquid nitrogen or the applied cooling substance and below the freezing temperature of water ice; further mixing with a steady increase of temperature above the freezing point of water; and further kneading/mixing of the homogeneously wetted mixture.

BRIEF DESCRIPTION OF THE FIGURES

FIG. 1 depicts a method of homogeneous wetting of at least one biopolymer, comprising: mixing of at least one biopolymer, ice in microparticular form, and optionally at least one active pharmaceutical ingredient by means of mechanical energy input to obtain a homogenous mixture at a temperature below the freezing point of water; further mixing the at least one biopolymer, ice in microparticular form, and optionally the at least one active pharmaceutical ingredient with a steady increase of temperature above the freezing point of water; and further kneading/mixing to produce a homogeneously wetted biopolymer.

FIG. 2 depicts a method of homogeneous wetting of at least one biopolymer, comprising: mixing of at least one biopolymer in dry form, ice produced by freezing water, dry ice ($CO_2$), and optionally at least one active pharmaceutical ingredient by means of mechanical energy input to obtain a homogeneous microparticular mixture of all ingredients at temperatures above the freezing temperature of dry ice and below the freezing temperature of water ice; further mixing with a steady increase of temperature above the freezing point of water; and further kneading/mixing of the homogeneously wetted mixture.

DESCRIPTION OF PREFERRED EMBODIMENTS OF THE INVENTION

Reference will now be made in detail to various aspects of the invention and embodiments. The following language and descriptions of certain preferred embodiments of the present invention are provided to further an understanding of the principles of the present invention. However, it will be understood that no limitations of the present invention are intended, and that further alterations, modifications, and applications of the principles of the present invention are also included.

All presented examples serve as illustrations of the inventions, and the examples are not restricted or limited to the materials used, or the process conditions or given applications that are used or described in the examples. All quantitative parameters are for illustrative purposes only and it is to be understood that different materials and process conditions can be used.

In accordance with the present invention, the terms polymer, biopolymer and derivations/modifications therefrom can include, but are not limited to, all biogenic (including biotechnological processes) macromolecules, proteins, polysaccharides, carbohydrates, nucleic acids, aptamers, collagen, collagen-n-hydroxysuccinimide, fibrin, gelatin, albumin, alginate, plasma proteins, milk proteins, whey proteins, caseins, protein-based polymers, hyaluronic acid, chitosan, pectin, gum arabicum, other gum-type representatives, agar, wheat protein, gluten, starch, cellulose, cellulose derivatives, plant materials, microorganism materials, lysate of cells, copolymers, mixtures or composites of all above mentioned components, and in addition, all artificial synthetic polymers composed of monomers of biogenic nature or occurrence. Also included are, for example, all occurring or imaginable composites of polymers and low-molecular weight compounds, including but not restricted or limited to surfactants, lipids, fatty acids, PEGs, oligomers of proteins, polysaccharides and nucleic acids, solubility-modifying compounds, peptides, amino acids, monosaccharides, disaccharides, and oligosaccharides.

In addition, without restriction or limitation, all inorganic compounds or any type of nano- or microparticles can be added/mixed to the polymeric plastic masses to provide composites, for example, hybrid composites.

Also, in accordance with the full scope of the present invention, there are also no restrictions or limitations with respect to the use of active and passive pharmaceutical, cosmeceutical or cosmetic ingredients or active and passive ingredients from the nutrition industries.

It is to be understood that the present invention contemplates certain representative methods and formulations, such as for example certain methods and formulations described herein, in which at least one active pharmaceutical ingredient is present.

It is also to be understood that the present invention also contemplates other representative methods, processes and formulations in which no active pharmaceutical ingredients are present or used at any point during the methods or processes, and therefore the present invention also contemplates formulations in which no active pharmaceutical ingredients are present in the final formulations. Therefore, when certain representative methods, processes and formulations are described herein, it is also to be understood that the present invention also contemplates that such methods, processes and formulations can be adapted or modified in an appropriate and suitable manner, as needed or desired, such that no active pharmaceutical ingredients are present or used at any point during the methods or processes, such that no active pharmaceutical ingredients are present in the final formulations.

Therefore it is to be understood that the methods and processes of the present invention, of which several examples are described herein, can be practiced and implemented in such a manner such that including at least one active pharmaceutical ingredient is optional.

The present invention not only covers the separation of wetting and mechanical mixing/kneading; the present invention also covers separating wetting and mixing of solvent with the material to be wetted. The present invention achieves an unprecedented homogeneity of wetting before even starting the kneading/mixing. Separation of wetting and kneading/mechanical mixing alone is not solving the problem, in principle, because all processes are carried out under solvent deficit and there is a competition of all material particles for the narrow resource of the wetting agent. Because of the inhomogeneous structure of the starting powder (huge total surface area of the particles constituting the powder) and the sub-optimum wetting this would result in a low quality of the plastic mass, especially if microscopic properties are taken into consideration (for example, inhomogeneous wetting). The present invention provides practical solutions to those problems and is illustrated by several examples.

The present invention provides processes that enable the development of products which represent a significant advancement over conventional approaches. The present invention also provides products at a higher qualitative level. For example, the processes of the present invention leads to very high quality microneedles and arrays thereof. The introduction of microneedles of highest quality can be utilized, for example, by the pharmaceutical industry.

The present invention provides novel and innovative methods which solves the aqueous solution wetting problem of concentrated polymer masses.

The present invention solves the core problem of many existing fabrication procedures, which is the insufficient and inhomogeneous local wetting of the polymer mass, by means of novel and innovative approaches. In preferred embodiments, the present invention provides novel and innovative approaches which separate wetting and mixing of the polymers with wetting liquids.

In contrast to conventional technical procedures, it has been found according to the present invention that the successful processing of macromolecules depends to a significant degree on the sequence of process steps as well as the dispersity of the polymer component.

An essential improvement in quality of preparation can be achieved by means of removal or reduction of concentration of gas/air in the process of wetting and subsequent kneading.

Preferred applications are hydrophilic matrices based on hyaluronic acid and/or chitosan, collagen, gelatin, alginate. Molecular weights and their distributions have to be adapted to respective applications.

Matrices can be prepared with and without pharmaceutical active ingredients.

Representative pharmaceutically active compounds or active pharmaceutical ingredients that can be used in accordance with the present invention include, but are not limited to, one or more immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists (e.g., anti TNF-alpha, Interleukin-1, Interleukin-6 etc.), antiangiogenic compounds (e.g., anti-VEGF, anti-PDGF etc.), intracellular signaling inhibitors (e.g. JAK1,3 and SYK inhibitors) peptides having a molecular mass equal to or higher than 3 kDa, ribonucleic acids (RNA), desoxyribonucleic acids (DNA), plasmids, peptide nucleic acids (PNA), steroids, corticosteroids, an adrenocorticostatic, an antibiotic, an antidepressant, an antimycotic, a [beta]-adrenolytic, an androgen or antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone and its synthetic or biosynthetic analogue, an immunosuppressant, an immunostimulant, a mitogen, a physiological or pharmacological inhibitor of mitogens, a mineralcorticoid, a muscle relaxant, a narcotic, a neurotransmitter, a precursor of a neurotransmitter, an oligonucleotide, a peptide, a (para)-sympathicomimetic, a (para)-sympatholytic, a protein, a sedating agent, a spasmolytic, a vasoconstrictor, a vasodilator, a vector, a virus, a virus-like particle, a virustatic, a wound-healing substance, and combinations thereof.

Besides delivery systems, such hydrophilic matrices can be designed as medical devices, for example, as clamps and binders, screws, stents, scaffolds etc., as illustrated by the examples/embodiments described below.

Active ingredients can be incorporated in the delivery systems and the systems can function for delivery purposes.

As described herein, it is to be understood that the present invention contemplates that in certain embodiments the temperature can be controlled by the interplay of dry ice, water ice and heat production via mechanical input. However, it is also to be understood that the present invention also contemplates that the temperature can be controlled in other embodiments by the use of liquid nitrogen for cooling purposes. Moreover, the present invention also contemplates that, in addition to liquid nitrogen, any other appropriate and suitable cooling substance can also be used which helps to control the temperature well below water's freezing point.

According to one embodiment, a method of homogeneous wetting of at least one biopolymer, comprises: mixing of at least one biopolymer in dry form, ice produced by freezing water, dry ice ($CO_2$) or liquid nitrogen or any other cooling substance and optionally at least one active pharmaceutical ingredient by means of mechanical energy input to obtain a homogeneous microparticular mixture of all ingredients at temperatures above the freezing temperature of dry ice or liquid nitrogen or the applied cooling substance and below the freezing temperature of water ice; further mixing with a steady increase of temperature above the freezing point of water; and further kneading/mixing of the homogeneously wetted mixture.

EXAMPLES

Manufacturing Example A

Components Include:
biopolymer as dry powder of microparticles
water ice in microparticular form
optional: active pharmaceutical ingredients
mixing of above given ingredients by means of mechanical energy input to obtain a homogenous mixture at temperatures below freezing point of water continuation of mixing with steady increase of temperature above the freezing point of water further kneading/mixing of the homogeneously wetted biopolymer Manufacturing Example B Components Include:
biopolymer in dry form
water in ice form
optional: active pharmaceutical ingredients
mixing of above given ingredients by means of mechanical energy input to obtain a homogeneous microparticular mixture at temperatures below the freezing point of water
continuation of mixing with steady increase of temperature above the freezing point of water
further kneading/mixing of the homogeneously wetted biopolymer Manufacturing Example C Components Include:
biopolymer in dry form
ice of water
dry ice ($CO_2$)
optional: active pharmaceutical ingredients
Mixing of all above given ingredients by means of mechanical energy input to obtain a homogeneous microparticular mixture of all ingredients at temperatures above the freezing temperature of dry ice and below the freezing temperature of water ice
continuation of mixing with steady increase of temperature above the freezing point of water; and
further kneading/mixing of the homogeneously wetted mixture.

Manufacturing Example D

The Following Two Components are Prepared Separately:
microparticular powder of biopolymers and
microparticular ice of water
Both components are mixed together by means of mechanical energy input at temperatures below the freezing point of water
continuation as given under Manufacturing Examples A and B
optional: addition of dry ice ($CO_2$) as done in Manufacturing Example C Representative Example of Chemical Crosslinking
E Addition of a chemical crosslinker to given Example systems from A to D before starting the mechanical input. The crosslinking reaction is finished after final shaping of the manufactured mixture.

Representative Example of Chemical Crosslinking
F

Addition of a chemical crosslinker to Example systems from A to D in the beginning or during the process of mechanical input mixing. The crosslinking reaction is finishing after final shaping of the manufactured mixture.

Representative Example of Chemical Crosslinking
G

Mechanical input mixing of systems according to Examples A to D.
Optional addition of a chemical crosslinker after most part of the mechanical input mixing is completed and/or transfer of the mixed mass into a system (liquid or gas) containing a chemical crosslinker which is taken up by diffusion/convection. Storage of the mass inside the system till completion (or wished degree of completion) of reaction.

Representative Example of Wetting via Gas Phase
H

Biopolymers or mixtures containing them according to the present invention without restriction can be given in separate form with respect to a wetting fluid phase. Under controlled condition (thermodynamic parameters like temperature, pressure, convection, radiation etc.) of these separate systems, solid biopolymer-containing phase and wetting fluid phase, a wetting process of the solid phase can be started and maintained by means of transfer of the wetting agent from the fluid phase through a communicating gas phase. This can provide a wetted polymer mass of different but adjusted degree of homogeneity of wetting. The fluid phase may also contain chemical crosslinkers which are transferred into the solid biopolymer-containing phase and may induce a crosslinking. Process start and extent may be controlled by thermodynamic parameters.

Representative Example of Sample Drying from Examples A bis H

Drying is done under static or dynamic conditions, with or without air or gas mixture convection, at temperatures below or above room temperature, under light or darkness. Crosslinked Samples of E to H can be treated (for example, by washing) before drying to remove, for example, non-reacting crosslinker.

Representative Example of Shaping of Polymer Masses (Plastic Masses) of Examples A to H All Samples of A to H can be shaped by means of standard procedures after mechanical energy input mixing without or under an early phase of crosslinking. For example, micro moulding procedures could provide microstructures. This shaping is applied to a still kneadable wet mass. After drying or fixation of the plastic mass all tools and procedures of precision mechanics can be applied (milling, laser treatment and shaping, drilling, shaping with a lathe, sticking, cutting etc.).

Representative Example of Storage of Plastic Masses of Examples A to D

The plastic masses can be further processed (for example, crosslinking, or drying) after manufacturing or stored in statu nascendi. The storage can be done in a manner to conserve the kneadable status of the smart and soft solid for a given period of time. This can be achieved by storage under high humidity and would keep the mass kneadable (like chewing gum consistency) for many weeks and months.

Representative Examples for Use of Plastic Masses from Examples A to H in Different Application Branches The kneadable (smart and soft) plastic material is composed of biopolymers and biopolymer mixtures, it can be formulated with and without crosslinking and can be stored and further processed under different humidity conditions.

Preferred application targets of the biopolymer products are medicine and cosmetics.

The above described manufacturing procedures, and modifications thereof, can be used for the following representative applications (these are just listed as non-limiting examples, and it is to be understood that these examples do not limit the scope of the present invention): buttons, buckles, insulators, combs, art pearls, several bodies and shells, for example, fountain pens, toys, chess pieces, dominos, checkers, brush body, manicure set tools, paper knife, plates, boxes, tooth rings, handholds, bijouterie, substitution of products from synthetic polymers, housewares, special systems with peculiar properties (for example, hyaluronic acid solutions of high concentration with and without crosslinking), tablets, matrices for tablets, solid dosage forms, medical devices, parts of medical devices, cosmetic products, microneedles, microneedle arrays, surface profiles by conformal coating.

Representative Examples for Use of Examples A to H as Microneedles/Microneedle Arrays The kneadable/smart soft plastic mass is composed of biopolymers and mixtures of biopolymers. It can be manufactured with and without crosslinking and can be stored in a kneadable form under different humidity conditions. Preferred application branches of the smart biopolymer masses are medicine and cosmetics.

The present invention also contemplates producing shaped microneedles by pressing the mass into micromoulds which are forming the negative (female) counterpart shapes of the microneedles. All possible geometric shapes (pyramid-type, cylindrical etc.) and sizes (height of the individual needle from 100 micrometer (for intradermal application) to 1000 micrometer (for transdermal application) of the microneedles and their arrays (distance of the needles, size of arrays etc.) are contemplated and can be fabricated (for example, via silicon, steel or ceramic moulds). The needles are made of, for example, hyaluronic acid or chitosan or mixtures therefrom or other biopolymers/mixtures. The molecular weights of the used biopolymers can be adapted to use conditions. Drying of the needles and, simultaneously, solidification can be done under different conditions, for example, maintenance of outer pressure or generation of vacuum, lyophilization, guiding humidity out of the solidifying arrays. The needle arrays are used for precision and personalized cosmetics and medicine. The properties of the microneedles can cover a wide range, from dissolvable to (nearly) not dissolvable, from payloaded with active ingredients to "empty" needles, with and without crosslinking, separable from or strongly fixed to a backing material.

As moulds there can be used silicon, metal, plastic or ceramic moulds. Needle geometry can be adapted to intra- or trans-dermal applications depending on the needle size (height). The microneedle arrays can be applied straight away or can be pressed to the skin for a given period of time by means of a plaster or bandage system.

The present invention also contemplates preparation of special microneedle arrays for topical application to the outer eye (for example, intra- or trans-scleral delivery). In this case, after applying the needles (for example, pure dissolvable hyaluronic acid material plus active ingredients) they can be made separable from the background plate.

Needle arrays can be applied to skin spots of mosquito bites and other burning or itching sites (for example, insect or tick bites, stinging nettles, etc.). They can also be applied to itching skin sites of dermatitis or neuro-dermatitis, acne or allergic spots.

The microneedles can comprise, for example, pure hyaluronic acid or pure chitosan, or, of mixtures of both. They can also be comprised of other biopolymers, and may optionally contain one or more pharmaceutical active ingredients.

Representative Examples for Use of Biopolymer Masses (Plastic Masses) from Examples A to H for Thin and Thick Films The kneadable material consists of biopolymers and mixtures therefrom described in above Examples. It can be formulated with or without crosslinking and can be stored under humidity and further processed later on.

The kneadable material can be shaped under pressure into thin and thick films of any size and shape. It can be dried in a subsequent process step.

These shaped films (from transparent to non-transparant depending on fabrication procedure) serve for cosmetic and pharmaceutical applications.

Modified films can be designed as foldable and rollable applications.

The films can be used for topical applications, for example, wound and skin dressings.

They can also be used for topical eye applications at the sclera.

Elastically deformable films can be used for internal human body applications/treatments, for example, dressings in cystic fibrosis, dressings in body cavities, intranasal applications, intravaginal applications, and applications using the opportunity/possibility of conformal coating, etc.

Representative Examples for Use of Biopolymer Mass (Plastic Mass) as Solid Body/Smart Solid Body The kneadable material consists of the above described biopolymers/biopolymer mixtures of the Representative Examples. It can be formulated with and without crosslinking and can be stored under different humidity conditions before further processing.

Preferred application branches of the biopolymer solid bodies are medicine and cosmetics.

In medicine the bodies can be applied as medical devices, surgical instruments and accessories, like screws, clamps, nails, knives, scissors, sewing kit components, fibres, tissues, arterial occlusion devices, powder.

In cosmetics these bodies can be used (but without restriction) as cosmetic spheres, combs, plates, masks, shaped bodies, dermaroller, lipsticks, sticks, powder.

Representative Examples of Use of Biopolymer Material According to Above Examples as Fibres, Filaments and Tissues The kneadable material consists of biopolymer mass (plastic mass) and mixed biopolymer mass as described in the Examples above. It can be formulated with and without crosslinking and can be stored under different humidity conditions before further processing.

Preferred application branches of the biopolymer solid bodies/smart bodies are medicine and cosmetics.

The biopolymer mass can be prepared in form of fibres and filaments which can be organized into tissues. All those forms can be used in medicine and cosmetics.

Representative Examples for Use of Biopolymer Materials According to Above Examples as Porous Materials and Solid Foam The kneadable plastic mass consists of biopolymers or their mixtures of above Examples. It can be formulated with and without crosslinking and can be stored under different humidity conditions before further processing.

Preferred application branches of porous materials and solid foams are medicine and cosmetics.

There can be fabricated porous bodies with air/gas-filled pores, their internal to external surface ratio can be very high leading to solid foams of extremely small material density. These foams can be applied in medicine and cosmetics, for example, wound dressings, scaffolds.

Representative Examples for Use of Biopolymer Mass (Plastic Mass) of Above Examples for Manufacture and Application of Inorganic-Organic Hybrid Systems The kneadable mass consists of biopolymer and mixtures therefrom described in above Examples. It can be formulated with or without crosslinking and can be stored under different humidity conditions before further processing.

Preferred application branches of the biopolymer solid bodies/smart bodies are in medicine and cosmetics.

The inorganic components of the hybrid composites comprise inorganic salts or inorganic micro- and nanoparticles of functional inorganic materials with properties like magnetism, electrical conductivity, catalytic activity, pigments, porosity, etc. They may determine the properties of the hybrid composites.

The formulated hybrid systems can be applied in medicine and cosmetics.

EXAMPLES

Example 1: Adaptation of Homogenization of Wetting

1A. Equal mass fractions of hyaluronic acid powder and water are put into a vessel and mixed by hand-shaking.

1B. Equal mass fractions of hyaluronic acid powder and water are put into the reaction vessel of an IKA Tube-Mill. This mixture is milled (2 times 20 seconds at 20,000 rpm).

1C. Equal mass fractions of hyaluronic acid powder and water ice macroscopic bodies are put into the reaction vessel of an IKA Tube-Mill. This mixture is milled (2 times 20 seconds at 20,000 rpm) under destruction/breaking up of the water ice.

Based on these steps, from 1A to 1B to 1C, an increase in homogenization of wetting of the mixture was observed, and it is concluded that this occurs from an increasing loss in macroscopic structure and clustering after milling/mixing.

Example 2: Pronounced Homogenization of Wetting

Equal mass fractions of hyaluronic acid powder and micronized water ice (water ice microparticles) together with one half mass fraction of dry ice are put into the reaction vessel of a firing pin mill (Cryogenic impact grinder with self-contained liquid nitrogen tub, SPEX CertiPrep Freezer Mill 6770, GBM Industry & Technology Group Co., Ltd). The mixture is milled under liquid nitrogen. The procedure provides a very homogeneous water-wetted hyaluronic acid mass.

Example 3: Solid Hyaluronic Acid Body Based on Homogeneously Wetted Hyaluronic Acid Mass 2 grams of sodium hyaluronate, 2 grams of frozen water ice (de-ionized) and a few grams of dry ice are milled 3 times for 1 minute at 10 oscillations per second (SPEX CertiPrep Freezer Mill 6770, GBM Industry & Technology Group Co., Ltd) under liquid nitrogen. The resulting hyaluronic acid mass was pressed into a silicon mould, taken out after a few minutes and dried. There was observed a shrinkage and mass loss under drying for 16 hours from 1.51 grams to 1.25 grams. The shaped solid body was extremely hard but not brittle.

Example 4: Crosslinked Hyaluronic Acid Solid Body After Homogeneous Wetting Under Cryomilling with Frozen Solution of Crosslinker (BDDE—Butanediol Diglycidyl Ether) and Subsequent Continuation of Crosslinking of the Homogenous Wetted Mass 1 ml of BDDE is mixed with 500 mg of acetic acid and further diluted with 6 ml of de-ionized water. This solution is frozen by addition of dry ice. To this system there is added 5 grams Natriumhyaluronat. This solid mixture is milled by means of an IKA Tube-Mill for 2 minutes at 25,000 rpm. The resulting homogenously wetted mass is pressed into a silicon mould. For completion of the crosslinking this system is put into a thermobox at 60 degree centigrade for 2 days keeping a steady pressure. After 2 days the crosslinked and shaped body was removed from the mould, weighed and transferred into de-ionized water to follow the swelling. After 3 days in de-ionized water the diameter of the shaped body as well as its mass (weight) have increased: diameter has increased by a factor of 1.2 referred to the starting value and mass has developed from 1.28 grams (start) to 2.66 grams (after 3 days). The swollen and shaped body is semi-transparent and of strong solid consistency.

Example 5: Hyaluronic Acid Solid Body Crosslinked by Means of Trimetaphosphate and Mixed Under Frozen Conditions 2.14 grams sodium hyaluronate and 1.12 g sodium trimetaphosphate are mixed for 1 minute by means of an IKA Tube-Mill at 25,000 rpm. Thereafter, there are added 3 grams of an aqueous 0.1 M NaOH solution together with a few gram of dry ice. The mixture is freezing and milled for 2 minutes under conditions given above. The resulting homogeneously wetted mass is pressed into a silicon mould and is stored for 16 hours under steady pressure in a thermobox at 60 degrees centigrade. After 16 hours the crosslinked and shaped body is removed from the mould, is weighed and put into de-ionized water for swelling. After 3 days in de-ionized water the diameter of the shaped body as well as its mass (weight) have increased: diameter has increased by a factor of 3.0 based on the starting value and mass has developed from 1.80 g (start) to 15.44 g (after 3 days). The swollen and shaped body is transparent and it conserved its shape.

The invention claimed is:

1. A method of homogeneously wetting a biopolymer, comprising:
mixing at least one biopolymer in the form of a dry powder, frozen aqueous ice, and optionally at least one active pharmaceutical ingredient, the mixing occurring by mechanical energy input to obtain a homogenous mixture at a temperature below the freezing point of the aqueous ice, wherein the at least one biopolymer and frozen aqueous ice are mixed in a range of about 40-50% biopolymer by mass;
further mixing the homogenous mixture of the at least one biopolymer, frozen aqueous ice, and optionally the at least one active pharmaceutical ingredient, the mixing occurring along with a steady increase of temperature to above the freezing point of the aqueous ice; and then
further kneading and/or mixing to produce a homogeneously wetted biopolymer,
wherein the at least one biopolymer comprises a polysaccharide, hyaluronic acid, sodium hyaluronate, chitosan, alginate, or any combination thereof.

2. The method of claim 1, wherein the at least one biopolymer comprises hyaluronic acid or sodium hyaluronate.

3. The method of claim 1, wherein the at least one biopolymer is a polysaccharide.

4. The method of claim 1, comprising mixing equal mass fractions of the at least one biopolymer and the frozen aqueous ice.

5. The method of claim 1, further comprising:
molding the homogeneously wetted biopolymer into a mold array having a shape of a microneedle; and
drying the molded microneedle.

6. The method of claim 1, further comprising fabricating the homogeneously wetted biopolymer into a film.

7. The method of claim 1, further comprising fabricating the homogeneously wetted biopolymer into a shaped solid body.

8. The method of claim 1, wherein the optional at least one active pharmaceutical ingredient is present.

9. The method of claim 8, wherein the at least one active pharmaceutical ingredient is selected from the group consisting of: immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compounds, intracellular signaling inhibitors peptides having a molecular mass equal to or higher than 3 kDa, ribonucleic acids, deoxyribonucleic acids, plasmids, peptide nucleic acids, steroids, corticosteroids, an adrenocorticostatic, an antibiotic, an antidepressant, an antimycotic, an adrenolytic, a beta-adrenolytic, an androgen, an antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug, an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone or its synthetic or biosynthetic analogue, an immunosuppressant, an immunostimulant, a mitogen, a physiological or pharmacological inhibitor of mitogens, a mineralocorticoid, a muscle relaxant, a narcotic, a neurotransmitter, a precursor of a neurotransmitter, an oligonucleotide, a peptide, a sympathomimetic, a parasympathomimetic, a sympatholytic, a parasympatholytic, a protein, a sedating agent, a spasmolytic, a vasoconstrictor, a vasodilator, a vector, a virus, a virus-like particle, a virustatic, a wound-healing substance, and combinations thereof.

10. The method of claim 1, wherein mixing the at least one biopolymer in the form of a dry powder, frozen aqueous ice, and optionally at least one active pharmaceutical ingredient further comprises mixing in a biopolymer crosslinker.

11. A method of homogeneously wetting a biopolymer, comprising:
mixing at least one biopolymer in the form of a dry powder, frozen aqueous ice, and at least one of dry ice ($CO_2$), liquid nitrogen, or any other cooling substance having a freezing temperature below that of the frozen aqueous ice, and optionally at least one active pharmaceutical ingredient, the mixing occurring by mechanical energy input to obtain a homogeneous mixture at a temperature above the freezing temperature of the dry ice, liquid nitrogen, or other substance and below the freezing temperature of the aqueous ice, wherein the at least one biopolymer and frozen aqueous ice are mixed in a range of about 40-50% of biopolymer by mass;
further mixing, the mixing occurring along with a steady increase of temperature to above the freezing point of the aqueous ice; and then
further kneading and/or mixing to obtain a homogenously wetted biopolymer,
wherein the at least one biopolymer comprises a polysaccharide, hyaluronic acid, sodium hyaluronate, chitosan, alginate, or any combination thereof.

12. The method of claim 11, wherein the at least one biopolymer comprises hyaluronic acid or sodium hyaluronate.

13. The method of claim 11, wherein the biopolymer is a polysaccharide.

14. The method of claim 11, comprising mixing equal mass fractions of the at least one biopolymer and the frozen aqueous ice.

15. The method of claim 11, further comprising:
molding the homogeneously wetted biopolymer into a mold array having a shape of a microneedle; and
drying the molded microneedle.

16. The method of claim 11, further comprising fabricating the homogeneously wetted biopolymer into a film.

17. The method of claim 11, further comprising fabricating the homogeneously wetted biopolymer into a shaped solid body.

18. The method of claim 11, wherein the optional at least one active pharmaceutical ingredient is present.

19. The method of claim 18, wherein the at least one active pharmaceutical ingredient is selected from the group consisting of one or more immunoglobulins, fragments or fractions of immunoglobulins, synthetic substance mimicking immunoglobulins or synthetic, semisynthetic or biosynthetic fragments or fractions thereof, chimeric, humanized or human monoclonal antibodies, Fab fragments, fusion proteins or receptor antagonists, antiangiogenic compounds, intracellular signaling inhibitors peptides having a molecular mass equal to or higher than 3 kDa, ribonucleic acids, deoxyribonucleic acids, plasmids, peptide nucleic acids, steroids, corticosteroids, an adrenocorticostatic, an antibiotic, an antidepressant, an antimycotic, an adrenolytic, a beta-adrenolytic, an androgen, an antiandrogen, an antianemic, an anabolic, an anaesthetic, an analeptic, an antiallergic, an antiarrhythmic, an antiarterosclerotic, an antibiotic, an antifibrinolytic, an anticonvulsive, an antiinflammatory drug an anticholinergic, an antihistaminic, an antihypertensive, an antihypotensive, an anticoagulant, an antiseptic, an antihemorrhagic, an antimyasthenic, an antiphlogistic, an antipyretic, a beta-receptor antagonist, a calcium channel antagonist, a cell, a cell differentiation factor, a chemokine, a chemotherapeutic, a coenzyme, a cytotoxic agent, a prodrug of a cytotoxic agent, a cytostatic, an enzyme and its synthetic or biosynthetic analogue, a glucocorticoid, a growth factor, a haemostatic, a hormone or its synthetic or biosynthetic analogue, an immunosuppressant, an immunostimulant, a mitogen, a physiological or pharmacological inhibitor of mitogens, a mineralocorticoid, a muscle relaxant, a narcotic, a neurotransmitter, a precursor of a neurotransmitter, an oligonucleotide, a peptide, a sympathomimetic, a parasympathomimetic, a sympatholytic, a parasympatholytic, a protein, a sedating agent, a spasmolytic, a vasoconstrictor, a vasodilator, a vector, a virus, a virus-like particle, a virustatic, a wound-healing substance, and combinations thereof.

20. The method of claim 11, wherein mixing the at least one biopolymer in the form of a dry powder, frozen aqueous ice, and at least one of dry ice ($CO_2$), liquid nitrogen, or any other cooling substance having a freezing temperature below that of the frozen aqueous ice, and optionally at least one active pharmaceutical ingredient further comprises mixing in a biopolymer crosslinker.

* * * * *